(12) United States Patent
Almirante

(10) Patent No.: US 10,988,438 B2
(45) Date of Patent: Apr. 27, 2021

(54) PROCESS FOR THE PREPARATION OF A NITRIC OXIDE DONATING PROSTAGLANDIN ANALOGUE

(71) Applicant: NICOX S.A., Valbonne (FR)

(72) Inventor: Nicoletta Almirante, Milan (IT)

(73) Assignee: NICOX S.A., Valbonne (FR)

( * ) Notice: Subject to any disclaimer, the term of this patent is extended or adjusted under 35 U.S.C. 154(b) by 0 days.

(21) Appl. No.: 16/967,057

(22) PCT Filed: Feb. 12, 2019

(86) PCT No.: PCT/EP2019/053455
§ 371 (c)(1),
(2) Date: Aug. 3, 2020

(87) PCT Pub. No.: WO2019/162149
PCT Pub. Date: Aug. 29, 2019

(65) Prior Publication Data
US 2021/0040032 A1     Feb. 11, 2021

(30) Foreign Application Priority Data
Feb. 21, 2018    (EP) ..................... 18157888

(51) Int. Cl.
*C07C 231/12*    (2006.01)
*C07C 405/00*    (2006.01)
(Continued)

(52) U.S. Cl.
CPC .......... *C07C 231/12* (2013.01); *C07C 201/02* (2013.01); *C07C 291/02* (2013.01); *C07C 405/0041* (2013.01); *C07C 405/00* (2013.01)

(58) Field of Classification Search
CPC ... C07C 231/12; C07C 201/02; C07C 291/02; C07C 405/00; C07C 405/0041
See application file for complete search history.

(56) References Cited

FOREIGN PATENT DOCUMENTS

| WO | 2009136281 A1 | 11/2009 | |
|---|---|---|---|
| WO | WO 2009/136281 | * 11/2009 | ....... C07C 405/0041 |
| WO | 2016155906 A1 | 10/2016 | |

OTHER PUBLICATIONS

International Search Report and Written Opinion issued in International Patent Application No. PCT/EP2019/053455 dated May 16, 2019.

* cited by examiner

*Primary Examiner* — Yate' K Cutliff
(74) *Attorney, Agent, or Firm* — Arent Fox LLP

(57) ABSTRACT

The present invention relates to a process for preparing the hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I).

(Continued)

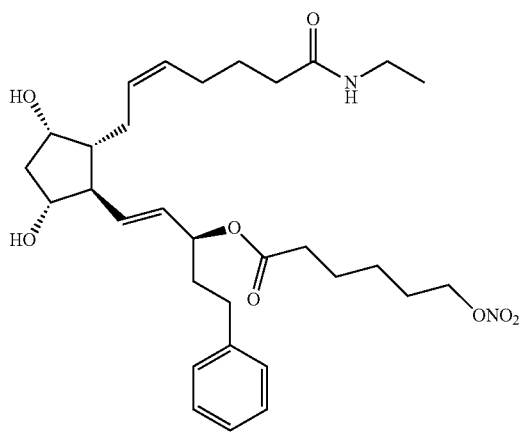

(I)

In accordance with the present invention, the compound (I) can be efficiently prepared with high purity by coupling bimatoprost in a boronate protected form with 6-(nitrooxy) hexanoyl chloride and removing the boronate protecting group.

The 6-(nitrooxy)hexanoyl chloride intermediate is prepared by ring-opening reaction of 2-caprolactone and subsequent nitration of the 6-hydroxyhexanoic acid potassium salt with a mixture of $HNO_3$ and $H_2SO_4$ in dichloromethane.

16 Claims, 3 Drawing Sheets

(51) Int. Cl.
  *C07C 291/02* (2006.01)
  *C07C 201/02* (2006.01)

PROCESS FOR THE PREPARATION OF A NITRIC OXIDE DONATING PROSTAGLANDIN ANALOGUE

This application is a 35 U.S.C. § 371 National Phase of PCT Application No. PCT/EP2019/053455, filed Feb. 12, 2019, which claims priority to European Patent Application No. 18157888.1, filed Mar. 21, 2018, the disclosures of which are hereby incorporated by reference herein in their entireties.

FIELD OF THE INVENTION

The present invention relates to an improved process for large scale preparation of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I).

BACKGROUND OF THE INVENTION

Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I)

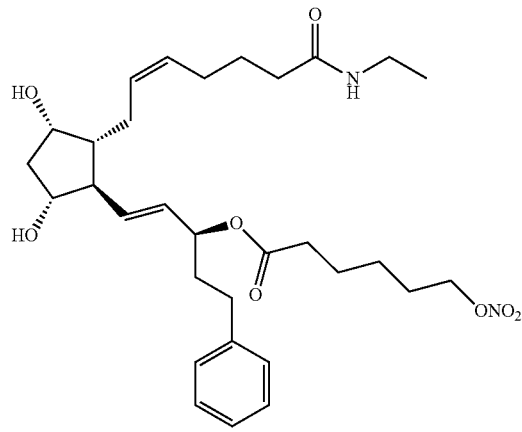

(I)

is a prostaglandin analogue that has proved effective as IOP-lowering agent (Impagnatiello F, Toris C B, Batugo M, Prasanna G, Borghi V, Bastia E, Ongini E, Krauss A H P; Invest Ophthalmol Vis Sci. 2015; 56:6558-64).

A process for preparing compound of formula (I) is disclosed in WO 2009/136281.

WO 2009/136281 specifically discloses the synthesis of compound (I) and in general the preparation of 15-alkyl nitrate esters of bimatoprost.

WO 2009/136281 discloses the synthesis of compound of formula (I) (Example B-1) by reacting bimatoprost in a boronate protected form (compound of formula (II)) with 6-bromohexanoyl chloride to give the 15-(6-bromohexanoyl) ester of bimatoprost in a boronate protected form (compound of formula (VIII)) that is converted into the nitrate derivative by silver nitrate in acetonitrile and deprotected/purified under reverse phase chromatography yielding compound of formula (I).

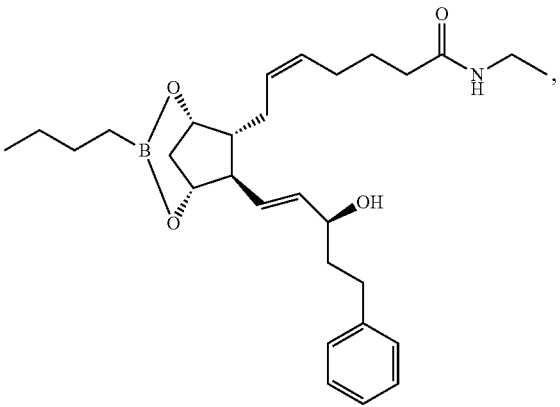

(II)

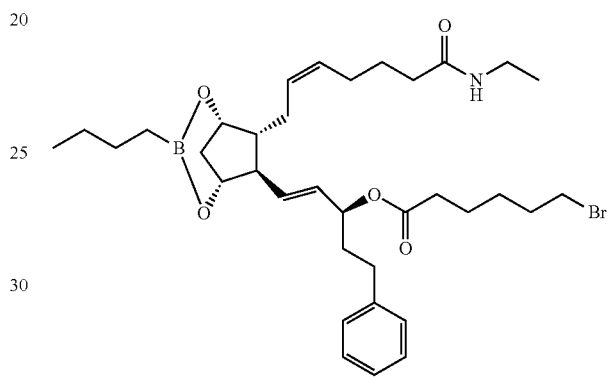

(VIII)

The main disadvantages of the above synthesis are the use in the esterification reaction of more than an equimolar amount of 6-bromohexanoyl chloride, which presents a structural alert for potential mutagenicity, and, in the last step, the use of silver nitrate that generates a large amount of silver salts in wastewater. Another main disadvantage of this process is the formation of impurities and by products such as 15-(6-bromohexanoyl) ester of bimatoprost (compound (IX)) and 15-(6-chlorohexanoyl) ester of bimatoprost (compound (X)) which are difficult to be removed even after multiple purifications, as they have similar polarity in chromatography, similar lipophilicity and/or solubility as those of compound (I).

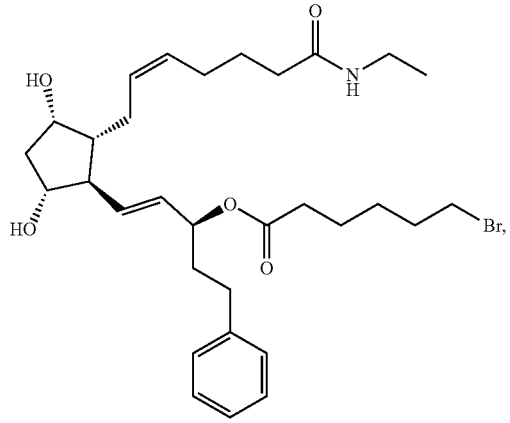

(IX)

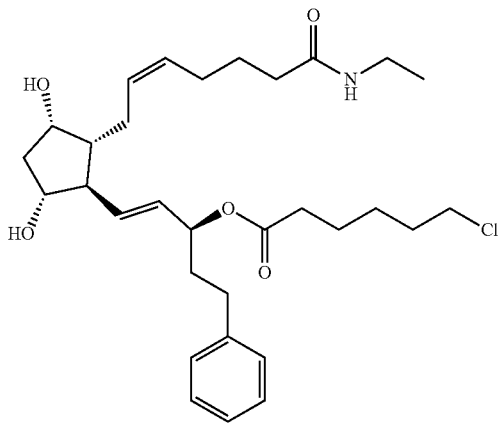

According to the procedure disclosed in WO 2009/136281, 15-(6-bromohexanoyl) ester of bimatoprost (compound (IX)) is an impurity deriving from uncompleted reaction of compound (VIII) with silver nitrate, after removal of the boronate protection. 15-(6-Chlorohexanoyl) ester of bimatoprost (compound (X)) is a by-product formed by halogen exchange reaction between the bromine atom of 15-(6-bromohexanoyl) ester of bimatoprost in a boronate protected form (compound (VIII)) and the free chlorine anion of 4-dimethylaminopyridine hydrochloride formed during the esterification step. The 15-(6-chlorohexanoyl) ester of bimatoprost in a boronate protected form (VIIIa) (FIG. 3—Scheme 3) does not react with silver nitrate and, after removal of the protective group, yields compound (X).

WO 2009/136281 also discloses an alternative process for the preparation of 15-acylalkynitrate bimatoprost derivatives (Examples N-1 and O-1). The synthesis comprises reacting bimatoprost in a boronate protected form (compound of formula (II)) with a nitrate-alkyl carboxylic acid chloride in the presence of 4-dimethylaminopyridine (DMAP) supported on resin (PS-DMAP), followed by removal of the boronate protecting group and purification using silica gel chromatography.

The above process avoids the use of 6-bromohexanoyl chloride and the removal of the silver salts from the final product. However, this method presents another main disadvantage that is the use of 4-dimethylaminopyridine supported on resin which makes the process unsuitable for commercial scale-up and expensive. Furthermore, nitrate-alkyl carboxylic acid chloride is added in two successive steps and in high excess with respect to compound of formula (II), indeed the alkyl carboxylic acid chloride is added in an amount from about 2 to 4 equivalents.

WO 2009/136281 also discloses another process (Examples Q1) for the preparation of 15-acylalkynitrate bimatoprost derivatives. In this process the compounds were obtained by esterification of bimatoprost in a boronate protected form (II) with an excess of nitrate-alkyl-(p-nitrophenyl)-carboxylate in the presence of 4-dimethylaminopyridine.

The removal of the unreacted nitrate-alkyl-(p-nitrophenyl)-carboxylate and of the by-product p-nitrophenol, formed in equimolar amounts to compound of formula (I), using chromatography methods are the main disadvantages of this process.

WO 2016/155906 discloses 15-nitrooxyderivatives of fluprostenol and it reports the synthesis of the 15-nitrooxy-hexyl ester of fluprostenol isopropyl ester. The compound was prepared by reacting fluprostenol isopropyl ester in a boronate protected form with (4-nitrophenyl)-6-nitrooxy-hexanoate in the presence of 4-dimethylaminopyridineexcess.

As reported above the removal of the unreacted nitrate-alkyl-(p-nitrophenyl)-carboxylate and, especially, the removal of the p-nitrophenol by-product by chromatography methods are the main disadvantages of this process.

In the past few years various regulatory authorities have been emphasizing on the purity requirements and the identification of impurities in the Active Pharmaceutical Ingredients (API). Currently, any impurity is considered as an organic material, besides the drug substance, that may influence the efficacy and safety of the pharmaceutical products. Therefore the identification of each impurity and the quantification of the impurities, especially those bearing structural alert for mutagenicity, have become a mandatory regulatory requirements. In addition, since the products are intended for pharmaceutical use, the range of industrially acceptable reagents, solvents, catalysts, etc. which can be used in the synthesis of the active ingredient is limited to those having pharmaceutical industry acceptability.

The compound of formula (I) is an oil and its purification in large scale quantities is difficult as it cannot be crystallized, therefore the presence of impurities is a critical issue for a large scale production. Since the main sources of impurities are the intermediates and the by-products of the synthesis, the purity of the intermediates and the control of the reactions conditions are important requirements for obtaining the final product having a pharmaceutical acceptable purity.

The prior art processes for the preparation of compound of formula (I) have some disadvantages; e.g. the use of bromohexanoyl chloride and the reaction conditions lead to the formation of the by-product 15-(6-chlorohexanoyl) ester of bimatoprost (compound (X)) that has a structural alert for potential mutagenicity; the use of silver nitrate for the preparation of the intermediate nitrate-alkyl carboxylic acid chloride or for the nitration of the 15-(6-bromohexanoyl) ester of bimatoprost in a boronate protected form (compound (VIII)) lead to the management of a large amount of silver nitrate wastewater, moreover metal content in the Active Pharmaceutical Ingredients must satisfy specific acceptance criterion.

Thus there is a need to provide compound of formula (I)) with high purity and in a good yield.

It has been found that compound of formula (I) can be prepared with high purity by using the 6-(nitrooxy)hexanoyl chloride intermediate efficiently prepared by ring-opening reaction of caprolactone followed by nitration.

The present invention provides a large scale production process that provides compound of formula (I) having a high chemical purity and, in particular, with a content of the 15-(6-chlorohexanoyl) ester of bimatoprost impurity below the safety level.

[(2Z)-7-(ethylamino)-7-oxo-2-hepten-1-yl]-3,5- dihydroxy-cyclopentyl]-1-(2-phenylethyl)-2-propen-1-yl ester (I) as described in Example 2.

DESCRIPTION OF THE INVENTION

Object of the present invention is a process for the preparation of hexanoic acid, 6-(nitrooxy)-, (1S,2E)-3-[(1R, 2R,3S,5R)-2-[(2Z)-7-(ethylamino)-7-oxo-2-hepten-1-yl]-3, 5-dihydroxycyclopentyl]-1-(2-phenylethyl)-2-propen-1-yl ester of formula (I):

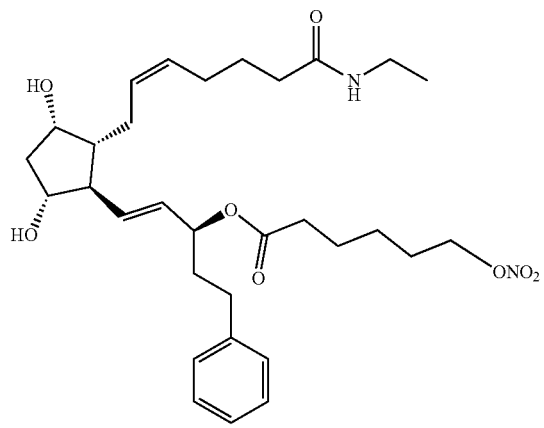

(I)

said process comprising the following steps:
a) reacting compound of formula (II):

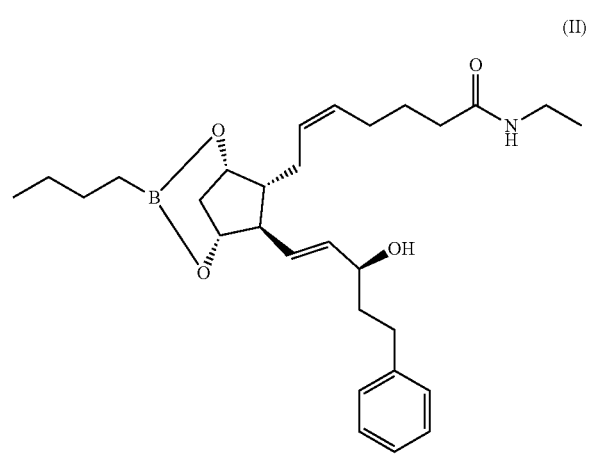 [SMILES: CCCCB1O[C@H]2C[C@@H](O1)[C@H](/C=C/[C@@H](O)CCc1ccccc1)[C@H]2C/C=C\CCCC(=O)NCC]

(II)

with 6-(nitrooxy)hexanoyl chloride of formula (IV):

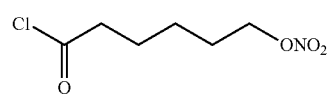

(IV)

in the presence of 4-dimethylaminopyridine in free form, to obtain compound of formula (III):

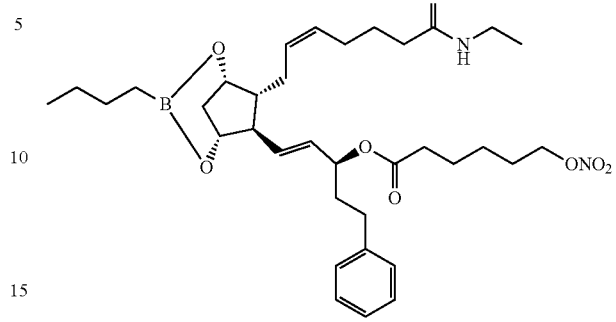

(III)

b) removing the boronate protective group of compound of formula (III) to obtain compound of formula (I).

4-Dimethylaminopyridine (DMAP) in free form means DMAP not bound to a resin.

Step a) is preferably carried out in an aprotic organic solvent, preferably selected from methyltertbutyl ether, N,N-dimethylformamide or dichloromethane. Most preferably the organic solvent is methyltertbutyl ether.

The molar ratio of compound of formula (II) to 6-(nitrooxy)hexanoyl chloride of formula (IV) preferably ranges from 1:1.4 to 1:1.6.

The molar ratio of compound of formula (II) to 4-dimethylaminopyridine preferably ranges from 1:2.0 to 1:2.4.

The reaction of step a) is carried out at a temperature ranging from 0° C. to room temperature.

The removal of the boronate protecting group (step b) is preferably carried out by reaction with methanol at a temperature from 17° C. to 24° C.

6-(Nitrooxy)hexanoyl chloride of formula (IV) is preferably obtained by a process comprising the following steps:
i) reacting 2-caprolactone of formula (V):

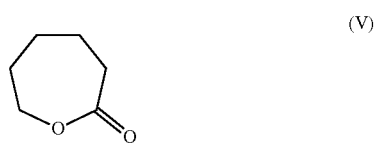

(V)

with an inorganic base selected from KOH, NaOH and LiOH to obtain 6-hydroxyhexanoic acid salt of formula (VI):

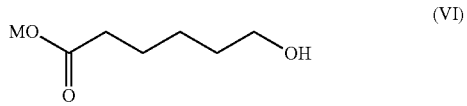

(VI)

wherein M is K, Na or Li.
ii) nitrating compound of formula (VI) with a mixture of $HNO_3$ and $H_2SO_4$ to obtain 6-(nitrooxy)hexanoic acid of formula (VII)

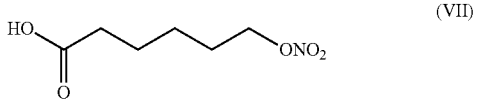

iii) converting 6-(nitrooxy)hexanoic acid of formula (VII) with a chlorinating reagent to 6-(nitrooxy)hexanoyl chloride of formula (IV).

6-(Nitrooxy)hexanoyl chloride of formula (IV) obtained in step iii) may be directly reacted with compound of formula (II) in step a) without further purification.

The inorganic base used in step i) is preferably potassium hydroxide.

Step i) is preferably carried out in a solvent selected from methanol, ethanol or isopropanol, most preferably methanol.

Steps ii) and iii) are carried out in dichloromethane.

The chlorinating reagent used in step iii) is oxalyl chloride.

Compound of formula (II) is obtained by reacting bimatoprost with butylboronic acid. Preferably the reaction is carried out in methyltertbutyl ether as solvent.

Figure 1:
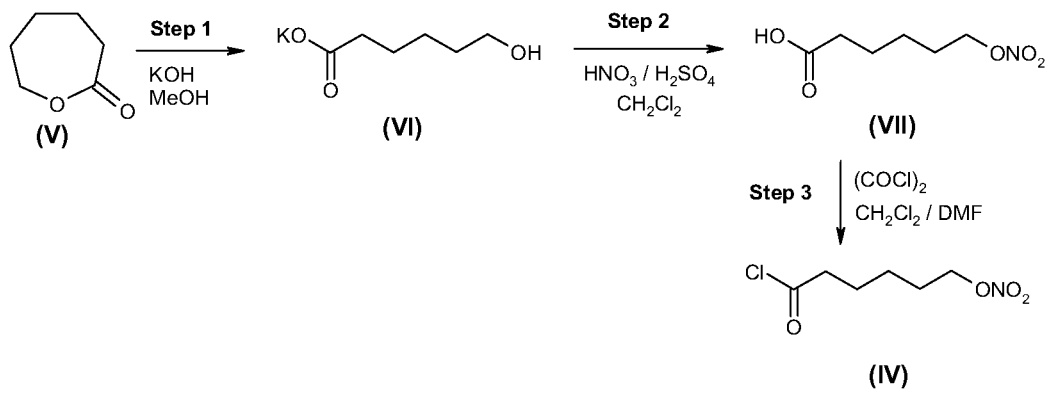
FIG. 1 shows Scheme 1 directed to the preparation of 6-(Nitrooxy)hexanoyl chloride (IV) as described herein.
Figure 2:
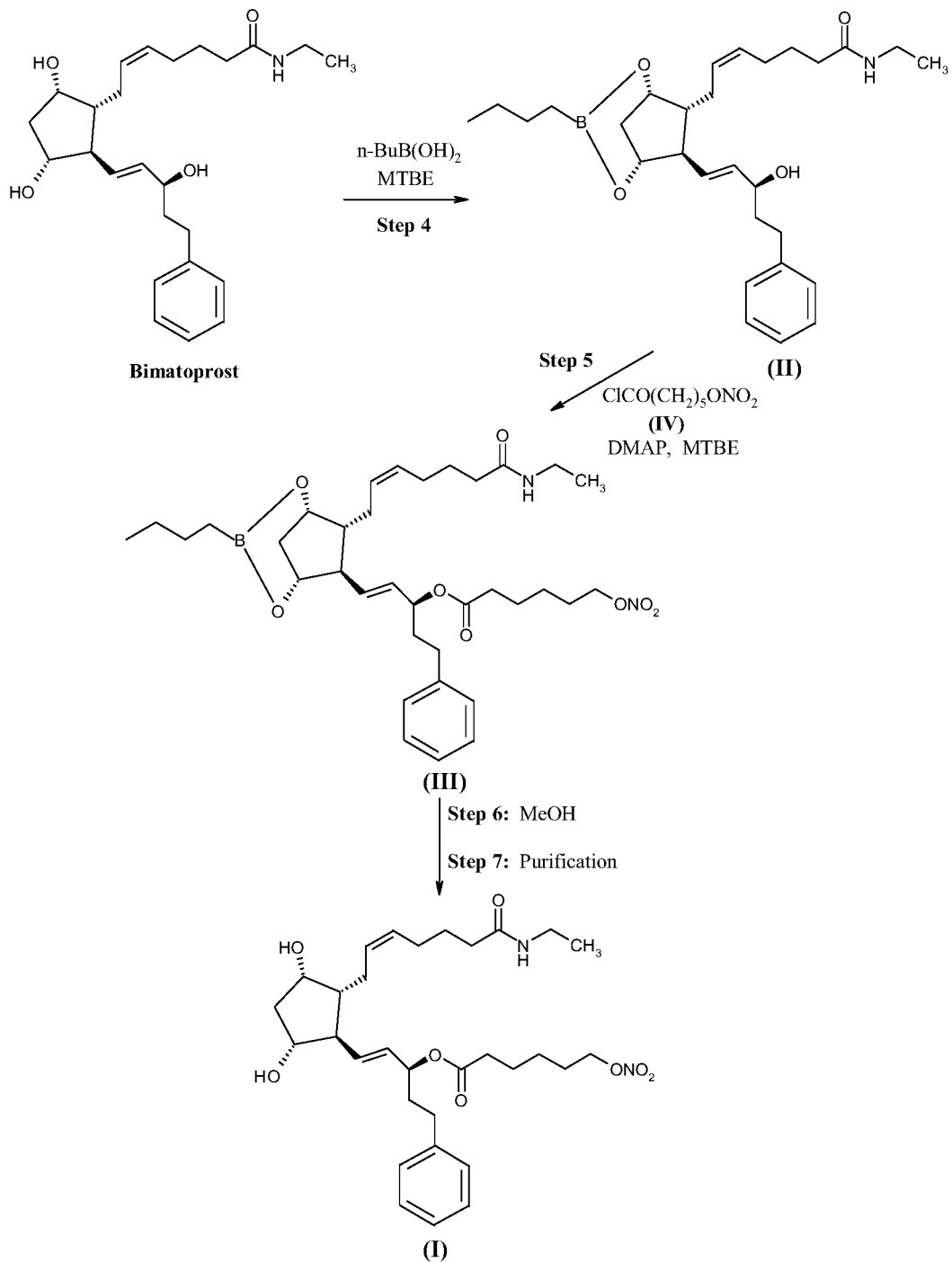
FIG. 2 shows Scheme 2 directed to the preparation of compound (I) as described herein.

A preferred process for the preparation of compound (I) is described in more details in Schemes 1 and 2 (FIGS. 1 and 2), said process comprising:

step 1) reacting 2-caprolactone of formula (V) with potassium hydroxide in methanol to obtain 6-hydroxyhexanoic acid potassium salt (compound of formula (VI) wherein M is potassium);

step 2) reacting 6-hydroxyhexanoic acid potassium salt with a mixture of $HNO_3$ and $H_2SO_4$ in dichloromethane to obtain 6-(nitrooxy)hexanoic acid (compound of formula (VII));

step 3) reacting 6-(nitrooxy)hexanoic acid with oxalyl chloride to obtain 6-(nitrooxy)hexanoyl chloride (compound of formula (IV)) that is used without further purification;

step 4) reacting bimatoprost with butyl boronic acid (1.1-1.8 eq) in methyltertbutyl ether (MTBE) at temperature around 40° C., then removing water by azeotropic distillation to obtain bimatoprost boronate (compound of formula (II));

step 5) reacting bimatoprost boronate (compound of formula (II)) with 6-(nitrooxy)hexanoyl chloride (IV), (1.4-1.6 equivalent) in methyltertbutyl ether in the presence of 4-dimethylaminopyridine (2.0-2.4 equivalent) at a temperature ranging from 0° C. to about room temperature, to obtain the compound of formula (III); step 6) reacting compound of formula (III) with methanol at room temperature for removal of protective group to obtain the crude compound of formula (I));

step 7) purifying the crude compound of formula (I) to obtain compound (I) having a chemical purity above 99%.

The process of the invention is characterized in that the 6-(nitrooxy)hexanoyl chloride (compound (IV)) intermediate is prepared with high chemical purity and high yield by ring-opening reaction of 2-caprolactone.

The experimental procedures of the steps of the process of the invention are described in detail below. All steps are run under nitrogen atmosphere.

6-(Nitrooxy)hexanoyl chloride (IV) is prepared in high purity and high yield starting from 2-caprolactone (FIG. 1—Scheme 1); the synthesis comprises the following steps:

step 1) a solution of potassium hydroxide (1 equivalent) in methanol is dropwise added to a solution of 2-caprolactone (1 equivalent) in methanol; the mixture is cooled at about 5° C. to 20° C. and stirred for about 5 hours at 15° C. to 20° C. after the addition is over; the solvent is removed (temperature is equal to or below 40° C.), the crude product is slurred in methyltertbutyl ether, 6-hydroxyhexanoic acid potassium salt (VI)) is filtered, washed with methyltertbutyl ether and dried. 6-Hydroxyhexanoic acid potassium salt (VI) was obtained with a 95% yield and a purity of 98.5% (H-NMR and HCl assay); step 2) 6-hydroxyhexanoic acid potassium salt (VI) (1 eq) is portion-wise added to a mixture of $HNO_3$ (4.6 eq) and $H_2SO_4$ (3.1 eq) in dichloromethane cooled at 0° C. to 5° C. under nitrogen in around 30 min while keeping the temperature below 10° C.; the resulting mixture is stirred around 2-3 hours at 0° C. to 10° C. monitoring the end of the reaction by $^1$H-NMR analysis; the mixture is cooled at a temperature from 0° C. to 5° C. and dropwise added with a saturated sodium chloride aqueous solution in around 20 min. The reaction mixture is maintained at a temperature below 10° C.; the organic layer is dried over anhydrous sodium sulfate, the solvent is removed to give 6-(nitrooxy)hexanoic acid (VII) in 86-88% yield and 97% HPLC purity;

step 3) N,N-dimethylformamide and oxalyl chloride are dropwise added to a solution of 6-(nitrooxy)hexanoic acid (VII) in dichloromethane, keeping the temperature of the solution from 0° C. to 5° C. for 1 hour, then the mixture is stirred at 15° C. to 30° C. for 24 hours; the solvent is evaporated off to obtain 6-(nitrooxy)hexanoyl chloride (IV) in 88-97% yield that is used without further purification.

The esterification process between bimatoprost and 6-(nitrooxy)hexanoyl chloride comprises the synthesis steps disclosed below:

step 4) bimatoprost is added to methyltertbutyl ether, and the resulting solution is cooled to about 15° C. to 18° C.; successively n-butyl boronic acid (1.11-1.18 equivalents) is added in one portion and the mixture is stirred for about 1-1.5 hour at 40° C. The end of the reaction is monitored by $^1$H NMR analysis; the reaction mixture is cooled down to about 20° C. to 25° C., filtered and the formed water is removed by azeotropic distillation of methyltertbutyl ether at a temperature equal to or below 40° C., until water content is below or equal to 0.25%, to give crude bimatoprost boronate (II) which is directly used in the next step;

step 5) crude bimatoprost boronate is added to methyltertbutyl ether and the resulting solution is cooled to about 0° C. to 5° C., 4-dimethylaminopyridine (about 2.1-2.3 equivalent) is added, 6-(nitrooxy)hexanoyl chloride (compound (IV)) (1.5 equivalent) dissolved in methyltertbutyl ether is dropwise added keeping the temperature of the mixture at about 0° C. to 5° C. After the addition, the mixture is stirred at about 0° C. to 5° C. up to 4 hours then overnight up to 15° C. to 20° C.; the end of the reaction is monitored by HPLC analysis; (1S,2E)-3-{(6R,7R)-3-butyl-7[(2Z)-7-(ethylamino)-7-oxohept-2-en-1-yl]-2,4-dioxa-3-borabicyclo [3.2.1]oct-6-yl}-1-(2-phenylethyl)-prop-2-en-1-yl-6-(nitrooxy) hexanoate (compound (III)) is isolated by standard work up methods (an example of work up is described in Example 1);

steps 6) compound (III) is dissolved in methanol and the resulting solution is stirred for about 18 hours at 17° C. to 25° C.; the conversion of compound (III) to compound (I) is monitored by $^1$H NMR. In case the reaction stops, the mixture is evaporated and re-dissolved in fresh methanol until complete conversion; the reaction mixture is then concentrated under vacuum at a temperature below 40° C. and the crude compound (I) is isolated by standard methods of work up;

step 7) the obtained crude product (I) is purified by column chromatography using a silica gel column and a mixed solvent of dichloromethane and methanol to give compound (I) with an overall yield of above 60% from bimatoprost and purity above 99%.

The process of the invention provides compound of formula (I)) in high yield and purity while reducing the amount of by-products, in particular the amount of (S,E)-1-((1R,2R,3S,5R)-2-((Z)-7-(ethylamino)-7-oxohept-2-enyl)-3,5-dihydroxycyclopentyl)-5-phenylpent-1-en-3-yl 6-chlorohexanoate (compound (X)) that has a structural alert for potential mutagenicity).

The above advantages make the process of the invention a cost effective process easily transferable to the industrial scale.

EXAMPLES

All synthesis steps described below were conducted under nitrogen atmosphere.

Example 1

Synthesis of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (I) (Batch 1)

Synthesis of 6-(nitrooxy)hexanoyl chloride (IV)

Step 1: Synthesis of 6-hydroxyhexanoic acid potassium salt (Compound (VI))

A solution of potassium hydroxide (131.9 g, 0.98 eq.) in methanol (1250 ml, 5 vol.) was prepared under cooling at 15° C. to 20° C. 25 0 g of 2-caprolactone (1 eq.) and methanol (625 ml, 2.5 vol.) was introduced in a 3 L three-necked round-bottomed flask. The mixture was stirred until dissolution. A methanol potassium hydroxide solution was added at 5° C. to 20° C. within 0.5 hour. The mixture was stirred for 4.5 hours at 15° C. to 20° C. The reaction mixture was concentrated under vacuum (at a temperature equal to or below 40° C.) to give crude 6-hydroxyhexanoic acid potassium salt (489.55 g). The crude was re-slurred in methyltertbutyl ether (1250 ml, 5 vol.) for 4 hours at 20° C. to 25° C., filtered on a pore 3 filter, washed with methyltertbutyl ether (2×250 ml, 2×1 vol.) and dried under vacuum at (temperature equal to or below 40° C.) to give 6-hydroxyhexanoic acid potassium salt (353.04 g) with 95.7% yield. Melting point 208° C. The product was analyzed by $^1$H-NMR and HCl assay.

Step 2: Synthesis of 6-(nitrooxy)hexanoic acid (VII)

This reaction is performed on a 100 g scale in order to control the reaction temperature and reducing the time of the addition of nitrating mixture. The reaction is repeated to obtain the necessary amount of 6-(nitrooxy)hexanoic acid.

Fuming $HNO_3$ (4.6 eq.) was added to concentrated $H_2SO_4$ (3.1 eq) at a temperature from 0° C. to 5° C. in 14 min, then $CH_2Cl_2$ (20 vol.) was added at a temperature from 0° C. to 5° C. in 12 min. 6-Hydroxyhexanoic acid potassium salt (101.29 g, 1 eq.) was added portion-wise in 28 min at temperature below 10° C. The mixture stirred for 2.2 hours at 0° C. to 10° C. and the reaction was monitored by H-NMR showing 99.9% conversion. The mixture was cooled to 0° C. to 5° C. and saturated sodium chloride aqueous solution (286.71 g in 910 mL, 10 vol.) was added carefully at a temperature equal to or below 10° C. within 17 min. After filtration of the insolubles, the organic layer was decanted, dried over sodium sulfate and concentrated under vacuum (at a temperature equal to or below 40° C.) to give 6-(nitrooxy)hexanoic acid with 87.7% yield and 97.0% HPLC purity.

Step 3: Synthesis of 6-(nitrooxy)hexanoyl chloride (IV)

6-(Nitrooxy)hexanoic acid (230 g, 1 eq.) was dissolved in dichloromethane (150 mL, 5 vol.). The resulting solution was filtered on a glass fibers, washed with dichloromethane (1×50 mL, 0.65 vol.) and analyzed by Karl Fischer (water content=0.016%). The filtrate was cooled to 0° C. to 5° C. under nitrogen. Subsequently N,N-dimethylformamide (1.35 mL, 0.0059 vol.) and oxalyl chloride (108.5 mL, 1 eq.) were added at 0° C. to 5° C. within 34 minutes. The reaction mixture was stirred at 0° C. to 5° C. for 3.5 hours and 14 hours at 15° C. to 20° C. TLC monitoring showed the complete reaction. The media was concentrated under vacuum (temperature is equal to or below 40° C.) and co-evaporated with dichloromethane (4×1 L, 4×4.35 vol.) to give 6-(nitrooxy)hexanoyl chloride (240.01 g) with 97.7% yield.

Step 4: Preparation of (Z)-7-[(1S,5R,6R,7R)-3-butyl-6-[((E,3S)-3-hydroxy-5-phenyl-pent-1-enyl]-2,4-dioxa-3-borabicyclo[3.2.1]octan-7-yl]-N-ethyl-hept-5-enamide (II)

Methyltertbutyl ether (2800 mL, 14 vol.) was charged in a flask. Bimatoprost (200 g, 1 eq.) was added and the equipment was rinsed with methyltertbutyl ether (200 mL, 1 vol.). Butyl boronic acid (58.94 g, 1.13 eq.) was added to the resulting suspension in one portion, the equipment was rinsed with methyltertbutyl ether (200 mL, 1 vol.). The mixture was heated to 40° C. for 1 hour. The reaction was monitored by $^1$H NMR till conversion>97%.

The reaction mixture was cooled to 20° C. to 25° C., clarified on a glass filter and washed with methyltertbutyl ether (200 mL, 1 vol.). The filtrate was charged in the 4 L three-neck round bottomed flask, the equipment was rinsed with methyltertbutyl ether (100 mL, 0.5 vol.) and the media was heated at a temperature about 40° C. under vacuum for azeotropic distillation. Rinsing with methyltertbutyl ether and azeotropic distillation was continued till the water content of (Z)-7-[(1S,5R,6R,7R)-3-butyl-6-[((E,3S)-3-hydroxy-5-phenyl-pent-1-enyl]-2,4-dioxa-3-borabicyclo[3.2.1]octan-7-yl]-N-ethyl-hept-5-enamide (compound (II)) was equal to or below 0.25%. Compound of formula (II) was obtained with quantitative yield (281.22 g).

Step 5: Preparation of (1S,2E)-3-{(6R,7R)-3-butyl-7[(2Z)-7-(ethylamino)-7-oxohept-2-en-1-yl]-2,4-dioxa-3-borabicyclo[3.2.1]oct-6-yl}-1-(2-phenylethyl)-prop-2-en-1-yl 6-(nitrooxy) hexanoate (III)

Methyltertbutyl ether (3196 mL, 11.6 vol.) was charged in a 4 L three-neck round-bottomed flask under nitrogen. (Z)-7-[(1S,5R,6R,7R)-3-Butyl-6-[((E,3S)-3-hydroxy-5-phenyl-pent-1-enyl]-2,4-dioxa-3-borabicyclo[3.2.1]octan-7-yl]-N-ethyl-hept-5-enamide (compound (II)) (276.48 g crude, 1 eq.) was added, equipment was rinsed with methyltertbutyl ether (398 mL, 1.44 vol.). The resulting solution was analyzed by Karl-Fischer (water content=0.072%) and cooled to 0° C. to 5° C. 4-Dimethylaminopyridine (138.5 g, 2.27 eq.) was added in one portion. A solution of 6-(nitrooxy)hexanoyl chloride (172.6 g, 1.5 eq.) in methyltertbutyl ether (508 mL, 1.84 vol.) was added dropwise at 0° C. to 5° C. within 1 hour. The dropping funnel was rinsed with methyltertbutyl ether (32 mL, 0.12 vol.). After stirring for 24 minutes at 0° C. to 5° C., HPLC monitoring showed 97.8% conversion. The mixture was stirred at 15 to 20° C. for 14.5 hours. HPLC monitoring showed 99.8% conversion. The reaction mixture was cooled at 0° C. to 5° C. and deionized water (1351 mL, 4.89 vol.) was added within 20 minutes at a maximum temperature of 15° C.

The mixture was stirred for 5 minutes and decanted. Aqueous layer was analyzed then discarded. An aqueous solution of 1N hydrochloric acid was prepared by mixing deionized water (493 mL, 1.78 vol.) and 11.6 N hydrochloric acid (46.6 mL, 1.08 eq.).

Organic layer was washed with the hydrochloric acid solution. Aqueous layer was analyzed then discarded. Organic layer was washed first with deionized water (1351 mL, 4.88 vol) then with a saturated sodium chloride solution (3×1177 mL, 3×4.25 vol.) previously prepared by mixing deionized water (3530 mL, 12.8 vol.) and sodium chloride (1175 g, 425% w/w).

Aqueous layers (pH=4 after the last washing) were analyzed and discarded. Organic layer was dried over sodium sulfate (240 g, 86.8% w/w), washed with methyltertbutyl ether (481 mL, 1.74 vol.) and concentrated under vacuum to afford (1S,2E)-3-{(6R,7R)-3-butyl-7[(2Z)-7-(ethylamino)-7-oxohept-2-en-1-yl]-2,4-dioxa-3-borabicyclo[3.2.1]oct-6-yl}-1-(2-phenylethyl)-prop-2-en-1-yl 6-(nitrooxy)hexanoate (compound (III)) with quantitative yield (327 g).

Step 6: Synthesis of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (I) (crude compound)

(1S,2E)-3-{(6R,7R)-3-butyl-7[(2Z)-7-(ethylamino)-7-oxohept-2-en-1-yl]-2,4-dioxa-3-borabicyclo[3.2.1]oct-6-yl}-1-(2-phenylethyl)-prop-2-en-1-yl 6-(nitrooxy) hexanoate (compound (III)) (325.4 g crude, 1 eq.) was dissolved in methanol (2873 mL, 8.83 vol.). The resulting solution was charged in the flask and equipment was rinsed with methanol (918 mL, 2.82 vol.). The mixture was stirred at 17° C. to 24° C. for 2.40 hours monitoring the reaction by $^1$H-NMR. The mixture was stirred for 15 additional hours at 16° C. to 20° C. Since $^1$H-NMR monitoring showed no evolution, methanol was removed under vacuum at 35° C. to 40° C. Methanol (918 mL, 2.82 vol.) was added to the residue and the mixture was stirred at 20° C. to 25° C. for 4 hours. H-NMR monitoring showed 94.6% of conversion. The reaction mixture was concentrated under vacuum at a temperature below 40° C. The residue was dissolved in methyltertbutyl ether (3530 mL, 10.85 vol.). The resulting solution was washed with deionized water (1770 mL, 5.44 vol.). The aqueous layer (pH=7) was discarded. A solution of sodium chloride (1045 g, 321% w/w) in deionized water (3134 mL, 9.63 vol.) was prepared. Organic layer was washed with the sodium chloride solution (2×1567 mL, 2×4.82 vol.). Aqueous layers were discarded. Organic layer was dried over sodium sulfate (320 g, 98% w/w), washed with methyltertbutyl ether (640 mL, 1.97 vol.) and concentrated under vacuum at a temperature below 40° C. to afford crude compound (I) (292.77 g.) with quantitative yield.

Step 7: Purification of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (I)

The mixture obtained in step 6) (crude compound (I)) was divided into 4 portions and purified using silica gel column (750 g×4, 10.34 vol.) and dichloromethane/methanol as eluent with a gradient 100:0 to 95:5 on a Combiflash. The fractions were monitored by TLC and analyzed by HPLC (% area). Fractions with HPLC (% area)≥98% were mixed and concentrated under vacuum at equal to or below 50° C. to afford 188.83 g, of Compound (I) that were further charged in the 4 L three-neck round-bottomed flask and dissolved in absolute ethanol (1510 mL, 8 vol.), equipment was rinsed with absolute ethanol (378 mL, 2 vol.). Activated charcoal (19 g, 10%/w) was added and the mixture was stirred at 20° C. to 25° C. for 0.5 hour. The charcoal was filtered and washed with absolute ethanol (189 mL, 1 vol.). The filtrate was concentrated under industrial vacuum at 45° C. to 50° C. for 2 hours then under high vacuum at 45° C. to 50° C. for 5 hours. Monitoring by $^1$H NMR in DMSO-d6 showed no residual solvents.

Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (I) (174.4 g.) was obtained with 63% overall yield from compound (II). HPLC purity was 99.47%

Following the same procedure described in Example 1, other two batches (2 and 3) of compound of formula (I) were prepared, Table 1 below reports the purity of compound of formula (I) of the 3 batches and the overall yield from compound (II).

TABLE 1

| Batch | Starting amount of compound (II) | Final amount of Compound (I) | HPLC Purity | Overall yield with respect to compound (II) |
|---|---|---|---|---|
| 1 (Example 1) | 231.72 | 174.4 | 99.47 | 63% |
| 2 | 225.8 | 148 | 99.4 | 54.9% |
| 3 | 321.28 | 236 | 99.7 | 61.5% |

Example 2 (Comparative Example)

Figure 3:
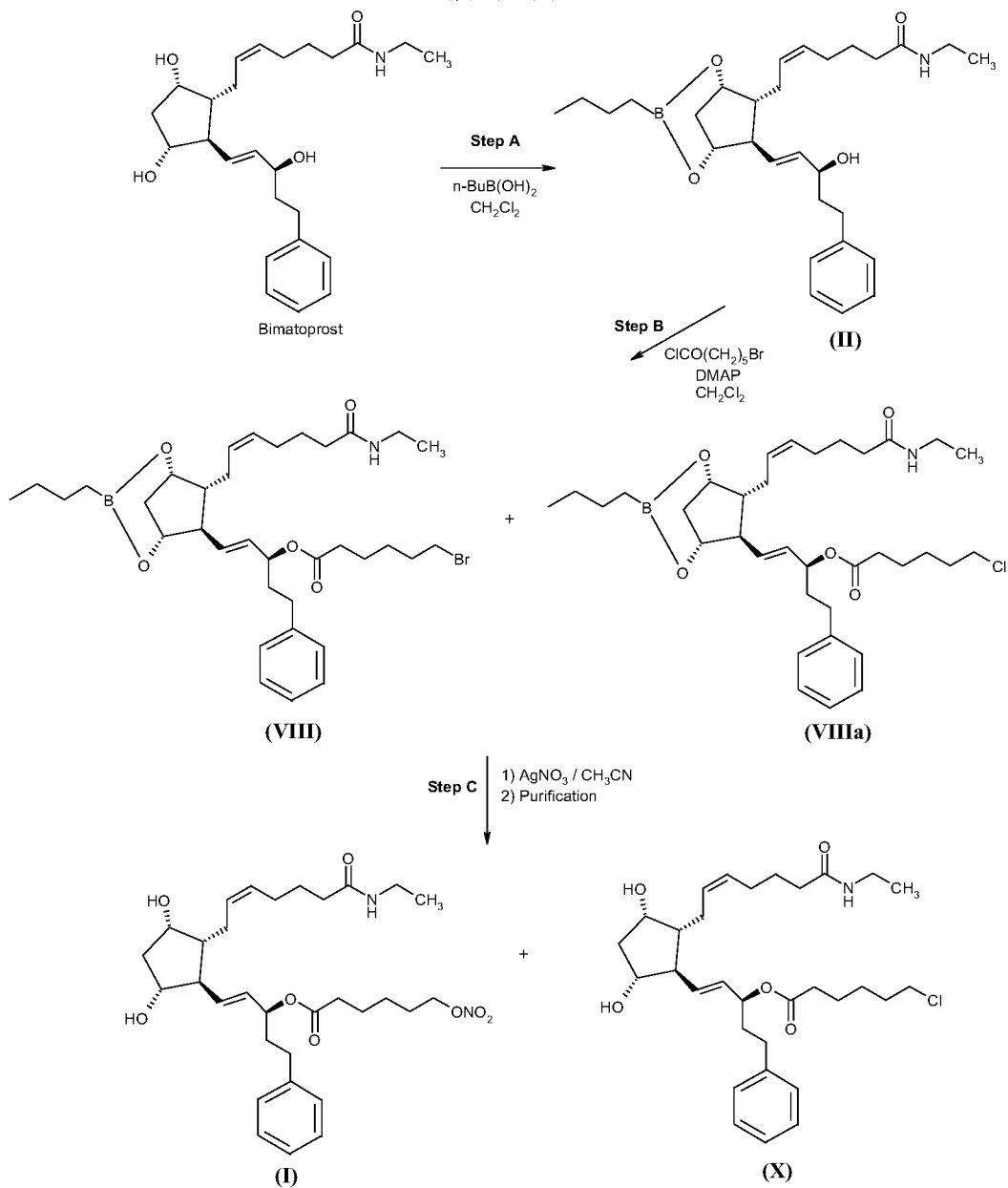
FIG. 3 shows Scheme 3 directed to the synthesis of hexanoic acid, 6-(nitrooxy)-, (1S,2E)-3-[(1R,2R,3S,5R)-2-

Synthesis of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (I) According to the Procedure Disclosed in WO 2009/136281 (FIG. 3—Scheme 3)

Step A: Preparation of (Z)-7-[(1S,5R,6R,7R)-3-butyl-6-[((E,3S)-3-hydroxy-5-phenyl-pent-1-enyl]-2,4-dioxa-3-borabicyclo[3.2.1)octan-7-yl]-N-ethyl-hept-5-enamide (II)

Butylboronic acid (1.129 eq.) was added to a solution of bimatoprost (1 g, 1 eq.) in dichloromethane (16 vol.). The mixture was heated to 40° C. for 1 hour, monitoring the progression of the reaction by $^1$H-NMR. Solvent was removed under reduced pressure for 2 hours. Dichloromethane (16 vol.) was added and the mixture was heated to 40° C. for another hour. Solvent was removed under pressure for 40 min. Dichloromethane (16 vol.) was added and the mixture was heated to 40° C. for 16 hours. Solvent was evaporated and the crude product was dried under high vacuum at 40° C. for 3 hours, yielding compound (II) in quantitative yield that was used in the next step without any further purification.

MS: m/z=438 [M+H]+

Step B: Synthesis of (S,E)-1-((1S,5R,6R,7S)-3-butyl-7-((Z)-7-(ethylamino)-7-oxohept-2-en-1-yl)-2,4-dioxa-3-borabicyclo[3.2.1]octan-6-yl)-5-phenyl-pent-1-en-3-yl 6-bromo hexanoate (VIII)

4-Dimethylaminopyridine (1.1 eq.) and 6-bromohexanoyl chloride (1.15 eq.) were added to a solution of compound (II) (0.8 g, 1 eq.) in dichloromethane (15.3 vol.) cooled to 0-5° C. The mixture was stirred for 0.5 hour at 0° C. to 5° C. and 16 hours at 20° C. to 25° C.

4-Dimethylaminopyridine (0.25 eq.) and 6-bromo-hexanoyl chloride (0.25 eq.) were added and the mixture was stirred for 19 additional hours. The reaction was monitored by $^1$H-NMR till complete conversion. The mixture was diluted with dichloromethane (15.3 vol.) and the organic solution was washed with deionized water (6.25 vol.) and brine (6.25 vol.). The organic phase was dried over $Na_2SO_4$ and concentrated under vacuum, to give compound (VIII) as a light yellow oil, (calculated as quantitative yield) used in the next step without further purification.

Step C: Synthesis of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (I)

Silver nitrate (3.72 eq.) was added to a solution of compound (VIII) (0.8 g, 1 eq.) in acetonitrile (9.4 vol.). The mixture was stirred for 18 hours at 20° C. to 25° C. The conversion was monitored by $^1$H-NMR in DMSO.

Silver nitrate (0.5 eq.) was added and the mixture was stirred for 20 additional hours until HPLC showed 99.7% conversion.

The mixture was filtered on a Whatman filter. The filtrate was concentrated under vacuum. The residue was dissolved in ethyl acetate (30 vol.). The organic phase was washed with deionized water (5 vol.) and brine (5 vol.). After drying over $Na_2SO_4$, the layer was concentrated under vacuum. The residue was chromatographed on silica gel column with dichloromethane/methanol 95:5 as eluent. The fractions were monitored by TLC and only fractions presenting one spot were mixed and concentrated under vacuum at a temperature equal to or below to 40° C. yielding compound (I) in 86% overall yield along with 4.27% of bimatoprost.

HPLC (% area) in reverse phase showed that purity of compound (I) was 77% and the

TABLE 2

| Example | | Compound (I) Overall Yield from compound (II) (%) | Purity of Compound (I) (%) | Impurities | Yield of Impurity (%) |
| --- | --- | --- | --- | --- | --- |
| 1 | Batch 1 | 63% | 99.47 | Comp. (X) | 0.16 |
|  | Batch 2 | 54.9% | 99.40 | Comp. (X) | 0.24 |
|  | Batch 3 | 61.5% | 99.76 | Comp. (X) | 0.15 |
| 2 |  | 86% | 77 | Comp. (X) | 8.34 |
|  |  |  |  | bimatoprost | 4.27 |

Table 2 reports the yield in Compound (I) and the main impurities formed during its preparation according to the process of the invention (Example 1) and to a method discloses in WO 2009/136281 (Example 2).

Compound (X)) is the 15-(6-chlorohexanoyl) ester of bimatoprost that has a structural alert for potential mutagenicity.

The results show that the process of the invention provides compound (I) having a chemical purity above 99% with a content of compound (X) from 0.15% to 0.26%, the process disclosed in the prior art leads to compound (I) having a chemical purity of 77% and a content of compound (X) of 8.34%, namely more than 30 fold higher than the amount of compound (X) formed in the process of the invention.

The results demonstrate that the process of the invention represents an improvement over the method described in the prior art.

The invention claimed is:

1. A process for the preparation of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester of formula (I):

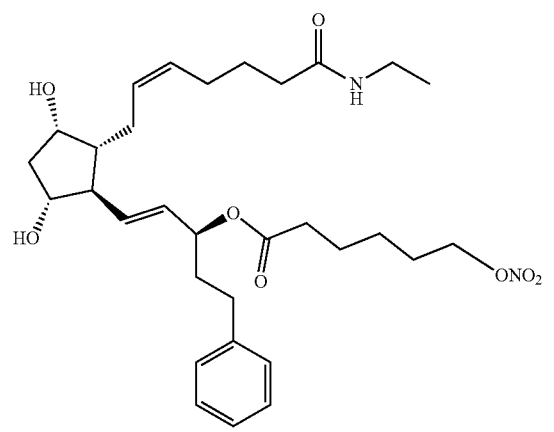

said process comprising the following steps:
a) reacting compound of formula (II):

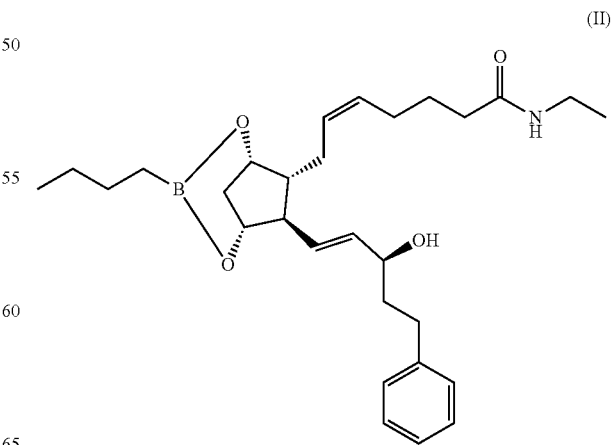

with 6-(nitrooxy)hexanoyl chloride of formula (IV):

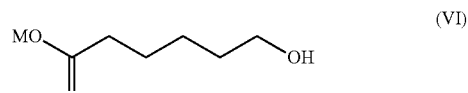
(IV)

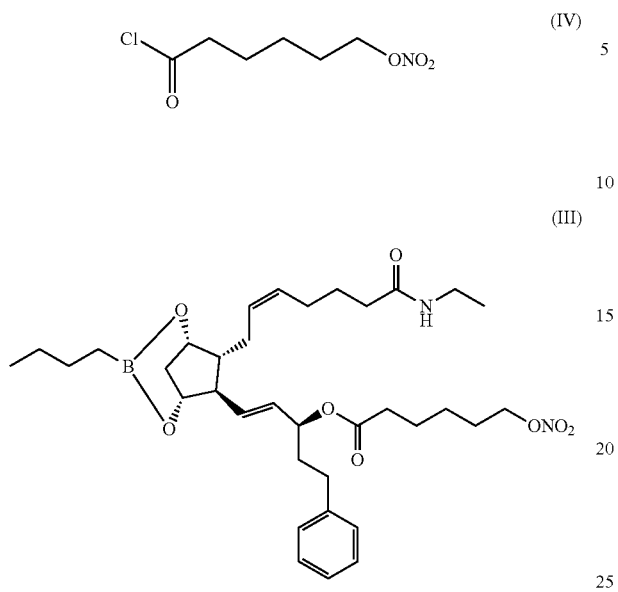
(III)

b) removing the boronate protective group of compound of formula (III) to obtain compound of formula (I).

2. The process according to claim 1 wherein step a) is carried out in an aprotic organic solvent.

3. The process according to claim 2 wherein the aprotic organic solvent is selected from methyltertbutyl ether, N,N-dimethylformamide or dichloromethane.

4. The process according to claim 3 wherein the aprotic organic solvent is methyltertbutyl ether.

5. The process according to claim 1 wherein in step a) the molar ratio of compound of formula (II) to 6-(nitrooxy)hexanoyl chloride of formula (IV) is 1:1.4 to 1:1.6 and the molar ratio of compound of formula (II) to 4-dimethylaminopyridine is 1:2.0 to 1:2.4.

6. The process according to claim 1 wherein step a) is carried out at a temperature ranging from 0° C. to room temperature.

7. The process according to claim 1 wherein 6-(nitrooxy)hexanoyl chloride of formula (IV) is obtained by a process comprising the following steps:

i) reacting 2-caprolactone of formula (V):

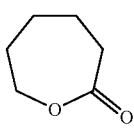
(V)

with an inorganic base selected from KOH, NaOH and LiOH to obtain 6-hydroxyhexanoic acid salt of formula (VI):

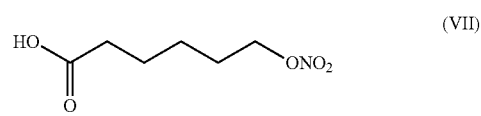
(VI)

wherein M is K, Na or Li, ii) nitrating compound of formula (VI) with a mixture of $HNO_3$ and $H_2SO_4$ to obtain 6-(nitrooxy)hexanoic acid of formula (VII)

(VII)

iii) converting 6-(nitrooxy)hexanoic acid of formula (VII) with a chlorinating regent to 6-(nitrooxy)hexanoyl chloride of formula (IV).

8. The process according to claim 7 wherein 6-(nitrooxy) hexanoyl chloride of formula (IV) obtained in step iii) is directly used in step a) without further purification.

9. The process according to claim 7 wherein the inorganic base used in step i) is potassium hydroxide.

10. The process according to claim 7 wherein step i) is carried out in a solvent selected from methanol, ethanol or isopropanol.

11. The process according to claim 10 wherein the organic solvent is methanol.

12. The process according to claim 7 wherein step ii) is carried out in dichloromethane.

13. The process according to claim 7 wherein step iii) is carried out by using oxalyl chloride as chlorinating reagent.

14. The process according to claim 7 wherein step iii) is carried out in dichloromethane.

15. The process according to claim 1 wherein compound of formula (II) is obtained by reacting bimatoprost with butylboronic acid.

16. A composition consisting of hexanoic, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester having a chemical purity above 99% and containing an amount of (S,E)-1-((1R,2R,3S,5R)-2-((Z)-7-(ethylamino)-7-oxohept-2-enyl)-3,5-dihydroxycyclopentyl)-5-phenylpent-1-en-3-yl 6-chlorohexanoate (compound (X)) from 0.15% to 0.26%.

* * * * *

UNITED STATES PATENT AND TRADEMARK OFFICE
CERTIFICATE OF CORRECTION

PATENT NO. : 10,988,438 B2
APPLICATION NO. : 16/967057
DATED : April 27, 2021
INVENTOR(S) : Nicoletta Almirante It is certified that error appears in the above-identified patent and that said Letters Patent is hereby corrected as shown below:

In the Claims

Column 15 (Claim 1), Line 9, insert -- in the presence of 4-dimethylaminopyridine in free form, to obtain compound of formula (III): --

Signed and Sealed this
Nineteenth Day of July, 2022

Katherine Kelly Vidal
*Director of the United States Patent and Trademark Office*